United States Patent
Govyadinov et al.

(10) Patent No.: US 12,102,998 B2
(45) Date of Patent: Oct. 1, 2024

(54) CELL SORTING DEVICES

(71) Applicant: HEWLETT-PACKARD DEVELOPMENT COMPANY, L.P., Spring, TX (US)

(72) Inventors: Alexander Govyadinov, Corvallis, OR (US); Viktor Shkolnikov, Palo Alto, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 745 days.

(21) Appl. No.: 17/297,219

(22) PCT Filed: Feb. 1, 2019

(86) PCT No.: PCT/US2019/016348
§ 371 (c)(1),
(2) Date: May 26, 2021

(87) PCT Pub. No.: WO2020/159542
PCT Pub. Date: Aug. 6, 2020

(65) Prior Publication Data
US 2022/0032298 A1    Feb. 3, 2022

(51) Int. Cl.
*B01L 3/00* (2006.01)
*B01F 23/00* (2022.01)
(Continued)

(52) U.S. Cl.
CPC ..... *B01L 3/502715* (2013.01); *B01L 3/50273* (2013.01); *B01L 3/502761* (2013.01);
(Continued)

(58) Field of Classification Search
CPC .. G01N 15/1484; G01N 15/01; G01N 15/149; G01N 2015/1493;
(Continued)

(56) References Cited

U.S. PATENT DOCUMENTS

| 6,540,895 B1 | 4/2003 | Spence et al. |
| 8,372,579 B2 | 2/2013 | Toner et al. |

(Continued)

FOREIGN PATENT DOCUMENTS

| EP | 2602608 B1 | 9/2016 |
| WO | WO-2005071097 A1 | 8/2005 |

(Continued)

*Primary Examiner* — Jennifer Wecker
*Assistant Examiner* — Oyeleye Alexander Alabi
(74) *Attorney, Agent, or Firm* — Foley & Lardner LLP

(57) ABSTRACT

In one example in accordance with the present disclosure, a cell sorting device is described. The cell sorting device includes a microfluidic channel to serially transport individual cells from a volume of cells along a flow path. A sensor disposed in the microfluidic channel distinguishes between a cell to be analyzed and waste fluid. The cell sorting device includes at least two fluid transport devices disposed within the microfluidic channel. The at least two fluid transport devices include a cell ejector to, responsive to detection of a cell to be analyzed, eject the cell to be analyzed from the cell sorting device and a waste transport device to direct the waste fluid to a waste reservoir.

13 Claims, 15 Drawing Sheets

(51) Int. Cl.
- *B01F 23/41* (2022.01)
- *B01F 101/23* (2022.01)
- *B01L 7/00* (2006.01)
- *B23Q 17/24* (2006.01)
- *C08J 3/075* (2006.01)
- *C08K 3/16* (2006.01)
- *C08K 3/22* (2006.01)
- *C08K 3/32* (2006.01)
- *C12Q 1/18* (2006.01)
- *G01N 15/01* (2024.01)
- *G01N 15/14* (2024.01)
- *G01N 15/149* (2024.01)
- *G01N 21/64* (2006.01)
- *G01N 27/411* (2006.01)
- *G01N 33/50* (2006.01)

(52) U.S. Cl.
CPC ............ B01L 7/52 (2013.01); G01N 15/1484 (2013.01); *B01L 2200/0652* (2013.01); *B01L 2200/0689* (2013.01); *B01L 2200/12* (2013.01); *B01L 2200/147* (2013.01); *B01L 2300/0663* (2013.01); *B01L 2300/1827* (2013.01); *B01L 2400/0442* (2013.01); *G01N 15/01* (2024.01); *G01N 15/149* (2024.01); *G01N 2015/1493* (2013.01)

(58) Field of Classification Search
CPC ....... G01N 2015/1006; G01N 15/1459; G01N 15/1404; B01L 2200/0652; B01L 2200/0689; B01L 2200/12; B01L 2200/147; B01L 2300/0663; B01L 2300/1827; B01L 2400/0442; B01L 2200/146; B01L 2300/0627; B01L 2300/0645; B01L 2300/0864; B01L 2400/0439; C12M 47/04

See application file for complete search history.

(56) References Cited

U.S. PATENT DOCUMENTS

| | | |
|---|---|---|
| 8,765,455 B2 | 7/2014 | Beer et al. |
| 8,820,538 B1 | 9/2014 | Lin |
| 9,604,214 B2 | 3/2017 | Foster et al. |
| 2002/0064809 A1 | 5/2002 | Mutz et al. |
| 2003/0148531 A1 | 8/2003 | Hatcher et al. |
| 2015/0024476 A1 | 1/2015 | Butler et al. |
| 2015/0196913 A1 | 7/2015 | Liu et al. |
| 2018/0043362 A1 | 2/2018 | Rogacs et al. |
| 2018/0056288 A1 | 3/2018 | Abate et al. |
| 2018/0133715 A1 * | 5/2018 | Craig ................. G01N 15/1492 |

FOREIGN PATENT DOCUMENTS

| | | | |
|---|---|---|---|
| WO | WO-2010001254 A2 | 1/2010 | |
| WO | WO-2017127119 A1 * | 7/2017 | .......... B01L 3/50273 |
| WO | WO-2018022026 A1 | 2/2018 | |

* cited by examiner

CELL SORTING DEVICES

CROSS-REFERENCE TO RELATED APPLICATIONS

This Utility Patent Application is a U.S. National Stage filing under 35 U.S.C. § 371 of PCT/US2019/016348, filed Feb. 1, 2019, incorporated by reference herein.

BACKGROUND

In analytic chemistry, scientists use instruments to separate, identify, and quantify matter. Cell lysis is a process of rupturing the cell membrane to extract intracellular components for purposes such as purifying the components, retrieving deoxyribonucleic acid (DNA), ribonucleic acid (RNA), proteins, polypeptides, metabolites, or other small molecules contained therein, and analyzing the components for genetic and/or disease characteristics. Cell lysis bursts a cell membrane and frees the inner components. The fluid resulting from the bursting of the cell is referred to as lysate.

BRIEF DESCRIPTION OF THE DRAWINGS

The accompanying drawings illustrate various examples of the principles described herein and are part of the specification. The illustrated examples are given merely for illustration, and do not limit the scope of the claims.

Figure 1:
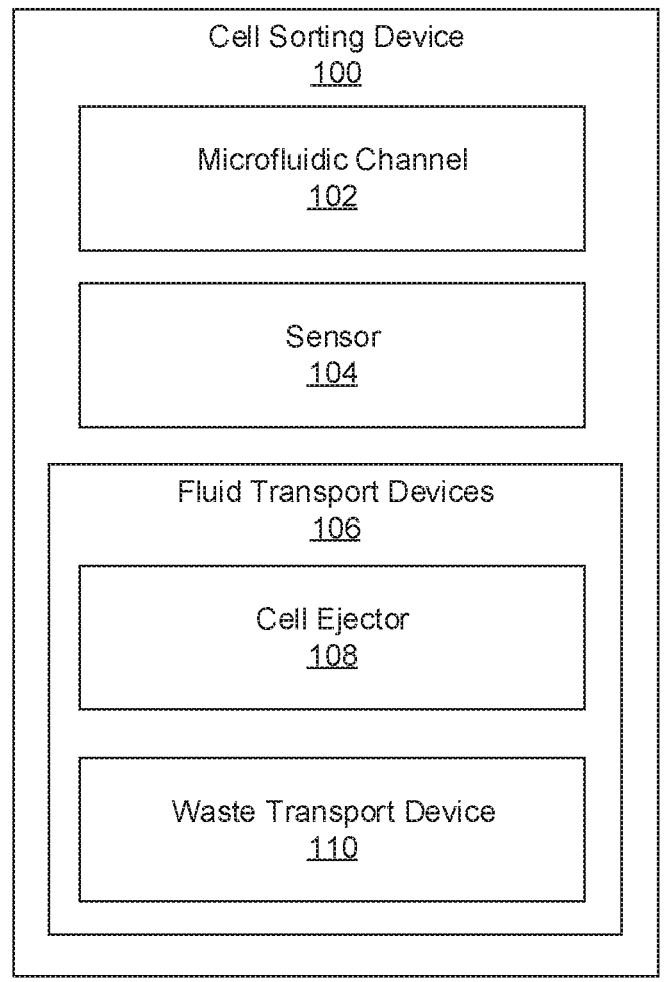
FIG. 1 is a block diagram of a cell sorting device, according to an example of the principles described herein.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION

Cellular analytics is a field of chemistry that uses instruments to separate, identify, and quantify matter. A wealth of information can be collected from a cellular sample.

However, before a cell can be analyzed, the cells in a sample are first sorted. That is, a sample may have a variety of different cells, and it may be desired to analyze a particular type of cell found within the sample. Accordingly, the sample is sorted such that the cells to be analyzed are separated from other cells and carrier fluid. Efficient cell sorting is helpful for a large number of applications. That is, in general, cell identification and sorting, by concentrating and characterizing individual cells enhances the accuracy of any subsequent analytic operation. As used in the present specification efficient cell sorting refers to cell sorting that is highly specific and has a high yield.

As a particular example, cells may be sorted during disease diagnoses, for example to detect tumorous cells for cancer diagnosis or by detecting bacterial cells for sepsis diagnosis. Sorting may also be used to research treatments. For example, by isolating certain cells for research and testing different treatment methods.

As yet another example, a blood sample may include blood cells and bacterial cells. A sorting system allows for differentiation of the bacteria cells and blood cells such that the bacteria cells can be analyzed without the influence of the blood cells in the population.

While a few specific examples have been provided, cells of a sample may be sorted for any number of reasons including distinguishing cells, differentiating cells, and detecting diseases to name a few. As cell sorting is a common, and relevant process in many cellular analytical applications, enhancements to its efficacy and simplicity may increase its value to cellular analytics.

For example, cells may be sorted optically using a fluorescence activated cell sorting (FACS) operation. In this example, marking is done manually in a separate vessel, with an excess of marking compound. In these operations, the marker may non-uniformly adhere to the cells. In this process, the cells are also exposed to atmosphere, which risks damage to the cells. Moreover, the systems that implement FACS are large, expensive, and do not lyse the cells.

FACS processes may take several hours with several manual operations. Cell lysis and any downstream analysis are therefore not correlated with the staining information, specifically on a single cell level. Moreover, as the time between sorting and lysing is long and certain biological cells may change over that period of time, any correlation that may be determined, is inconclusive and likely erroneous.

FACS operations also have a low yield and have a specificity that varies. For example, some FACS operations include cell labeling, in some cases by an antibody, which labeling introduces variability and error into the operation. This antibody labeling also changes the chemical profile of the cell as the cell responds to the antibody interaction. Moreover, FACS sorts cells in the aggregate and not individually, thus again introducing variability into any subsequent analysis and reducing a concentration of a desired cell matrix.

Another sorting mechanism is antibody-based cell selection using, for example, magnetic beads and columns. However, as with FACS, this magnetic assisted cell sorting (MACS), also includes labeling of the cells which leads to error and alters the molecular pathways occurring in the cells. Other methods also include density separation methods and membrane filtration. As an additional complication, many cell sorting systems rely on motion of the sorting device to separate cells from the carrier fluid.

Accordingly, the presently described cell sorting system addresses these and other issues. Specifically, the present specification describes a sorting device that is included on a microfluidic chip which can sort cells individually. The sorting device includes at least two fluid transport devices and at least one sensing element. The sensing element can discriminate particles based on at least one of particle size, impedance, color, fluorescence, and scattering response, among others. Cells to be analyzed are ejected to a downstream analytic device by action of a sensor-activated ejector.

Specifically, the present specification describes a cell sorting device. The cell sorting device includes a microfluidic channel to serially transport individual cells from a volume of cells along a flow path. A sensor disposed in the microfluidic channel distinguishes between a cell to be analyzed and waste fluid. The cell sorting device also includes at least two fluid transport devices disposed within the microfluidic channel. The at least two fluid transport devices include 1) a cell ejector to, responsive to detection of a cell to be analyzed, eject the cell to be analyzed from the cell sorting device and 2) a waste transport device to direct the waste fluid to a waste reservoir.

The present specification also describes a method. According to the method a quantity of cells is passed, in serial fashion, from a cell reservoir to at least one cell sorting device of a microfluidic cell analysis system. Then, for each cell sorting device, cells to be analyzed are detected, a cell ejector, when a cell to be analyzed is detected, is activated to eject the cell to be analyzed, and a waste fluid is directed to a waste reservoir.

In another example, a cell sorting system includes a cell reservoir to contain a volume of cells and multiple cell sorting devices. Each cell sorting device includes a microfluidic channel to serially transport individual cells along a flow path. Each cell sorting device also includes at least two fluid transport devices disposed within the microfluidic channel. The at least two fluid transport devices include 1) at least one cell thermal inkjet resistor to, responsive to detection by the sensor of a cell to be analyzed, eject the cell to be analyzed and 2) a waste thermal inkjet resistor to eject waste fluid through an orifice to a waste reservoir. The cell sorting system also includes a component controller to selectively activate the cell thermal inkjet resistor and the waste thermal inkjet resistor based on an output of the sensor.

In summary, using such a cell sorting device 1) allows single cell sorting of a sample; 2) uses fluid ejection to separate cells from carried fluid; 3) uses two separate ejection devices spatially separated from each other; 4) separates cells without use of an alteration inducing stain; and 5) simplifies the device integration into a larger system. However, the devices disclosed herein may address other matters and deficiencies in a number of technical areas.

Turning now to the figures, FIG. 1 is a block diagram of a cell sorting device (100), according to an example of the principles described herein. In some examples, the cell sorting device (100) is part of a single integrated device that is multi-functional. Such a device combines several laboratory functions on a single integrated circuit which may be disposed on a silicon wafer. Such devices may be a few square millimeters to a few square centimeters, and provide efficient small-scale fluid analysis functionality.

In other words, the components, i.e., the microfluidic channel (102), sensor (104), and fluid transport devices (106) may be microfluidic structures. A microfluidic structure is a structure of sufficiently small size (e.g., of nanometer sized scale, micrometer sized scale, millimeter sized scale, etc.) to facilitate conveyance of small volumes of fluid (e.g., picoliter scale, nanoliter scale, microliter scale, milliliter scale, etc.).

The microfluidic channel (102) delivers cells along a flow path. That is, the microfluidic channel (102) is the conduit through which the cells flow. In some examples, natural environmental conditions direct the flow. For example, the cell reservoir from which the cells originate may be disposed above the cell sorting device (100) such that the effects of gravity draw fluid along the flow path. In other examples, flow may be induced. That is, the fluid transport devices (106) or other pumps may push fluid along the flow path.

The microfluidic channel (102) passes the cells in individual fashion along the flow path. That is, the cell sorting device (100) of the present specification describes a per-cell sorting. Accordingly, the microfluidic channel (102) may have properties such that cells are passed individually. For example, such a serial, single-file introduction of cells along the flow path may be facilitated by a microfluidic channel (102) having a cross-sectional area size on the order of the cell diameter.

The cell sorting device (100) also includes a sensor (104) disposed within the microfluidic channel (102) to distinguish between a cell to be analyzed and waste fluid. That is, in general, the cell sorting device (100) is to sort those cells desired for downstream analysis from other cells in a cell sample. For example, a blood sample may include blood cells as well as bacterial cells. In this example, a scientist may wish to separate the cells such that the bacterial cells in isolation may be analyzed. Accordingly, the sensor (104) may distinguish between the bacterial cells and the blood cells such that bacterial cells may be passed for processing and the blood cells may be disposed of as waste fluid.

The sensor (104) may take many forms. For example, the sensor (104) may be an optical scatter sensor that identifies cells based on a scatter of reflected energy waves. The sensor (104) may be an optical fluorescence sensor (104) that identifies cells based on the detection of certain fluorescent markers. In other examples, the sensor (104) may be an optical bright field sensing system, an optical dark field sensing system, a thermal sensor, or a magnetic field sensor. For example, the thermal conductivity of a cell to be analyzed may be different enough from the surrounding fluid and/or different enough from other cells in the sample, that the sensor (104) may be able to detect such a difference.

In another example, the sensor (104) detects a marker placed on the cell to be analyzed. That is, through an upstream process, a marker may be attached to a cell, which marker may alter an optical and/or electrical property of a particular cell. As a specific example, the marker may be a fluorescent marker that fluoresces in the presence of certain components found on a particular cell to be analyzed. In this example, the sensor (104) may be particularly selected to detect the alteration imposed by the marker.

Other examples of sensors that may be used include a flow sensor which can detect a flow of fluid past the sensor along the flow path. A flow sensor when used in conjunction with other sensors can determine not only the presence of the cell to be analyzed, but can be used to determine when the cell to be analyzed is positioned in front of a cell ejector to expel the cell to be analyzed to a downstream component.

A pressure sensor is another example of the sensor (104). In this example, an increase in pressure may indicate the presence of a cell. That is, a first pressure value may exist when carrier fluid passes by the pressure sensor (104). However, as a cell passes by, the pressure may increase. The pressure increase is indicative of a cell at that point in the flow. Different changes in pressure indicate different cells. For example, larger cells will result in a larger pressure change as compared to smaller cells.

In one particular example, the sensor (104) is an impedance sensor. Specifically, the sensor (104) may include at least one pair of electrodes spaced apart from one another by a gap. These electrodes detect a level of conductivity within the gap. That is, carrier fluid in which cells are contained, have a predetermined electrical conductivity. Any change to the solution between the electrodes will effectively change the electrical conductivity. Specifically, as the cells pass between the electrodes, the conductivity between the electrodes changes as compared to when just carrier fluid was present between the electrodes.

Thus, in summary, the sensor (104), which may include one sensor (104) in the microfluidic channel (102), can determine when a cell is present in the flow path by distinguishing it from other cells based on at least one of a cell size, cell impedance, cell color, cell fluorescence, and a cell scattering response.

In an example, the cell sorting device (100) includes at least two fluid transport devices (106) disposed within the microfluidic channel (102). The fluid transport devices (106) are selectively activated based on an output of the sensor (104).

Specifically, one of the at least two fluid transport devices (106) is a cell ejector (108) to, responsive to detection of a cell to be analyzed, eject the cell to be analyzed from the cell sorting device (100). That is, the cell sorting device (100) may be disposed upstream of a cell analysis system. In this example, the cell sorting device (100) prepares the cell sample for analysis by the cell analysis system.

In some examples, the downstream analysis device may be formed in the same silicon substrate as the other components, albeit in a different chamber. In yet another example, the downstream analysis device may be a separate component, for example a well plate to which the cell is directed towards.

The cell ejector (108) may include a firing resistor or other thermal device, a piezoelectric element, or other mechanism for ejecting fluid from the firing chamber. For example, the cell ejector (108) may be a firing resistor. The firing resistor heats up in response to an applied voltage. As the firing resistor heats up, a portion of the fluid adjacent the firing resistor vaporizes to form a bubble. This bubble pushes the cell to be analyzed out an orifice and onto a surface such as a micro-well plate. As the vaporized fluid bubble collapses, a vacuum pressure along with capillary force draws additional fluid towards the cell ejector (108), and the process repeats. In this example, the cell ejector (108) may be a thermal inkjet ejector (108).

In another example, the cell ejector (108) may be a piezoelectric device. As a voltage is applied, the piezoelectric device changes shape which generates a pressure pulse that pushes a fluid out the orifice. In this example, the cell ejector (108) may be a piezoelectric inkjet ejector (108). In either of these examples, the cell ejector (108) may in part generate the flow throughout the microfluidic channel (102).

As described above, the cell ejector (108) operates responsive to an output of the sensor (104). That is, an output of the sensor (104) may selectively activate a particular cell ejector (108). When an output of the sensor (104) indicates the presence of a particular cell to be analyzed, the cell ejector (108) may be activated to eject that cell. Such a cell-based ejector activation allows for the precise distinction and separation of cells to be analyzed from other cells that are not relevant for a given cellular analytic operation.

Another of the fluid transport devices (106) is a waste transport device (110) that is also disposed in the microfluidic channel (102) and that directs waste fluid to a waste reservoir. Similar to the cell ejector (108), the waste transport device (110) may include a firing resistor or other thermal device, a piezoelectric element, or other mechanism for ejecting fluid from the firing chamber. Along with the cell ejector (108) operation of the waste transport device (110) in part generates the flow throughout the microfluidic channel (102).

In some examples, the waste transport device (100), like the cell ejector (108) is operated based on the output of the sensor (104). But in an alternate fashion. That is, in some examples, responsive to detection of a cell to be analyzed, the waste transport device (110) is deactivated. As an additional example of this case, responsive to a detection that a cell to be analyzed is not present, the waste transport device (110) is activated.

In another example, the waste transport device (110) operates independently of the sensor (104). That is, the schedule by which the waste transport device (110) operates to move or expel waste fluid is independent of any reading by the sensor (104). Doing so simplifies control circuitry as there is no hardware or instructions to control the waste transport device (110).

The cell sorting device (100) also includes an orifice through which the cell to be analyzed is ejected. That is, as described above, in some examples, the downstream analysis device may be formed in the same silicon substrate as the other components, albeit in a different chamber. In yet another example, the downstream analysis device may be a separate component, for example a well plate to which the cell is directed towards. Accordingly, the cells to be analyzed are ejected through the orifice to this downstream analysis device. Thus, the present cell sorting device (100) provides an effective and efficient cell sorting mechanism that provides a high yield, is single-cell based which increases the yield, and which does not contaminate or potentially damage the cells to be analyzed. Specifically, the sorting system separates the desired cell to be analyzed from other cells in the sample and/or the carrier fluid of the sample. Doing so provides a more concentrated solution of the cells.

Moreover, by excluding undesirable cell types from being analyzed, any results are more particularly mapped to the desired cell. That is, the results of an analysis of a particular cell would not be skewed by analysis of a disparate cell type.

Figure 2:
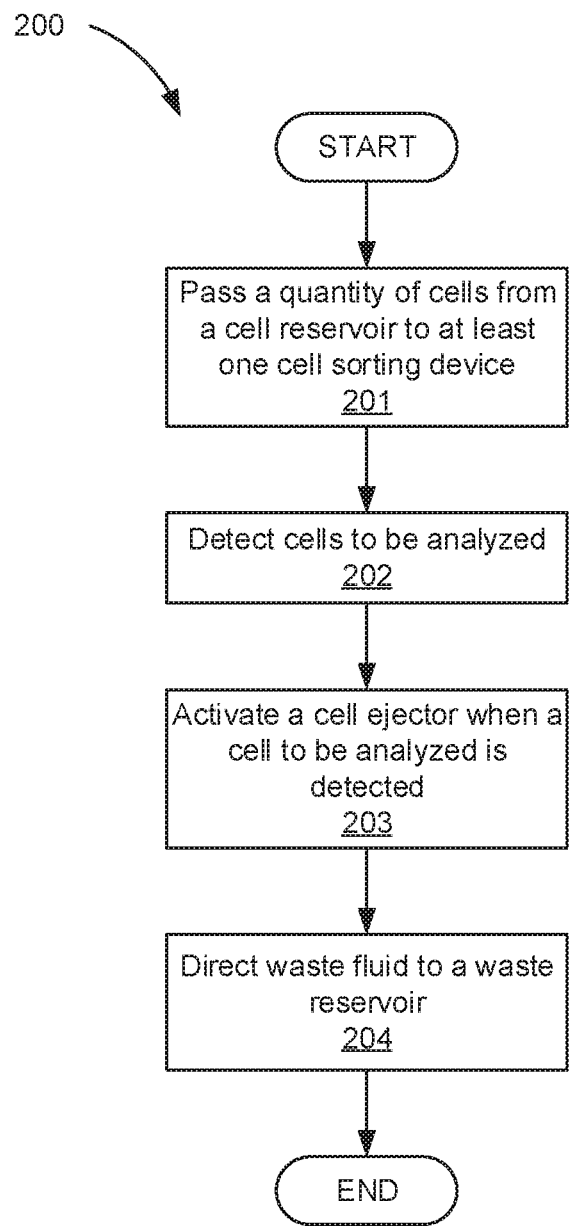
FIG. 2 is a flow chart of a method of cell sorting, according to an example of the principles described herein.

FIG. 2 is a flow chart of a method (200) of cell sorting, according to an example of the principles described herein. In the method (200), a quantity of cells to be analyzed are passed (block 201) from a cell reservoir to at least one cell sorting device (FIG. 1, 100) of a microfluidic system. That is, a cell sorting system may include one, or multiple cell sorting devices (FIG. 1, 100). Implementing multiple cell sorting devices (FIG. 1, 100) facilitates increased throughput by parallelizing the operations of the cell sorting devices (FIG. 1, 100). As described above, the cell sorting system (FIG. 1, 100) may be a microfluidic system.

In some examples, the quantity of cells is serially passed (block 201) to each cell sorting device (FIG. 1, 100). That is, each cell within the sample may be received (block 201) one at a time. In some examples, each cell sorting device (FIG. 1, 100) includes a microfluidic channel (FIG. 1, 102) that gates introduction of one cell at a time along the flow path. Such single-file, or serial, inlet of cells facilitates an individual sorting of cells. Accordingly, rather than sorting a group of cells and hoping that particular cells are separated as intended, individual cells can be treated such that it may be ensured that targeted cells are distinguished from others in the sample.

The subsequent operations may be performed per cell sorting device (FIG. 1, 100). Cells to be analyzed are detected (block 202) and distinguished from other cells or components of the solution in which they are disposed. That is, a sample may include a wide variety of cell types, only one of which may be targeted for further analysis. The detection (block 202) operation identifies these cells from others. This may be done by the sensor (FIG. 1, 104). The cells may be distinguished from other cells based on at least one of a cell size, a cell impedance, a cell color, a cell fluorescence and cell light scattering properties.

For example, different cells may have different sizes. The different size of the cells may result in a different pressure changes when passing by a particular point along the fluid path. In this example, the sensor (FIG. 1, 104) detects the magnitude of the pressure change and associates it with a particular size of cell. Thus, cells are distinguished based on their size.

In another example, different cells may have different electrical conductivity. An impedance sensor (FIG. 1, 104) can detect the different electrical conductivity and distinguish the cells accordingly. Thus, cells to be analyzed are detected (block 202) based on their impedance.

In another example, different cells may have different fluorescence. In some examples, the fluorescence of particular cell is based on a chemical reaction between the cell and a marker placed upon the cell. In this example, the sensor (FIG. 1, 104) detects the fluorescence of a particular cell and compares it to an expected fluorescence for cells to be analyzed. Detection (block 202) in this example is made when a detected fluorescence matches an expected fluorescence.

Optical properties may also be used to detect (block 202) cells to be analyzed. That is, cells to be analyzed may have a distinct color and/or light scattering response as compared to other cells. Accordingly, the sensor (FIG. 1, 104) may be an optical sensor (FIG. 1, 104) that can detect these particular distinct optical properties.

A cell ejector (FIG. 1, 108) is then activated (block 203) to eject the cell to be analyzed when a cell to be analyzed is detected. That is, the sensor (FIG. 1, 104) is disposed before the cell ejector (FIG. 1, 108) and may trigger activation of the cell ejector (FIG. 1, 108). For example, if the sensor (FIG. 1, 104) indicates that a cell is not present, a controller of the cell sorting system may avoid activating the cell ejector (FIG. 1, 108). By comparison, if the sensor (FIG. 1, 104) indicates that a cell is present, the controller may activate the cell ejector (FIG. 1, 108) immediately. In another example, the cell ejector (FIG. 1, 108) is activated following a predetermined amount of time based on the expected flow time between when the cell passes the sensor (FIG. 1, 104) and when the cell is expected to align with the cell ejector (FIG. 1, 108). As described above, the sensor (FIG. 1, 104) may not only detect whether a cell is present, but whether the cell is of a type intended to be analyzed.

In addition to ejecting the cell to be analyzed, the cell sorting device (FIG. 1, 100) directs (block 204) waste fluid to a waste reservoir. As will be described below this may include directing (block 204) the waste fluid to an integrated waste reservoir or directing (block 204) the waste fluid to an external waste reservoir on a separate substrate.

Figure 3:
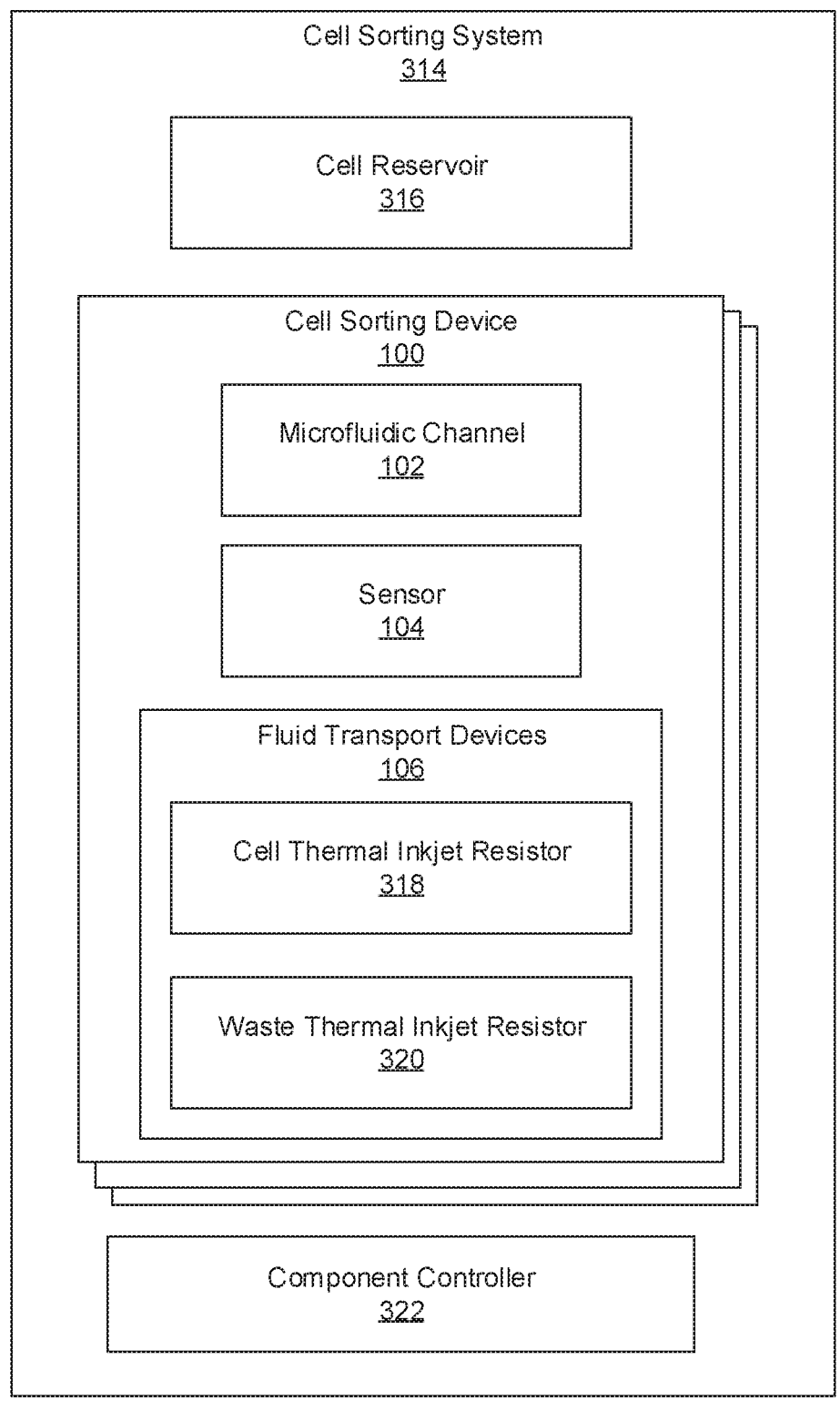
FIG. 3 is a block diagram of a cell sorting system, according to an example of the principles described herein.

FIG. 3 is a block diagram of a cell sorting system (314), according to an example of the principles described herein. In some examples, the cell sorting system (314) is part of a multi-function device, which may be referred to as a lab-on-a-chip device. A lab-on-a-chip device combines several laboratory functions on a single integrated circuit which may be disposed on a silicon wafer. Such multi-function devices may be a few square millimeters to a few square centimeters, and provide efficient small-scale fluid analysis functionality.

In other words, the components, i.e., the cell reservoir (316) and cell sorting devices (100) may be microfluidic structures. A microfluidic structure is a structure of sufficiently small size (e.g., of nanometer sized scale, micrometer sized scale, millimeter sized scale, etc.) to facilitate conveyance of small volumes of fluid (e.g., picoliter scale, nanoliter scale, microliter scale, milliliter scale, etc.).

First, as described above the cell sample may be retained in a cell reservoir (316), which may be any container or receptacle to hold a sample of cells to be analyzed by a cell analysis system. The cell reservoir (316) may be coupled to each of multiple cell sorting devices (100).

Specifically, the cell sorting system (314) includes multiple cell sorting devices (100). Using multiple cell sorting devices (100) facilitates increased throughput. That is, as described above, each cell sorting device (100) operates on a single cell at a time. Accordingly, using multiple cell sorting devices (100) parallelizes the operation such that instead of acting on one cell at a time, multiple cells may be treated, although still on an individual basis.

Each cell sorting device includes a microfluidic channel (102) to serially transport individual cells from the cell reservoir (316) along a flow path. While traveling along the flow path, each cell passes by a sensor (104) which distinguishes between a cell to be analyzed and the waste fluid. Each sorting device also includes at least two fluid transport devices (106) disposed within the microfluidic channel (102). A first may be a cell thermal inkjet resistor (318) which, responsive to detection by the sensor (104) of a cell to be analyzed ejects the cell to be analyzed. The ejection may be onto any desired substrate, such as a well plate for subsequent analysis.

The second may be a waste thermal inkjet resistor (320) which ejects waste fluid through a waste orifice to a waste reservoir. That is, in this example, the waste reservoir may be off-chip and thus the waste fluid is ejected from the cell sorting system (314) into a waste receptacle.

The cell sorting system (314) also includes a component controller (322) to selectively activate the cell thermal inkjet resistor (318) and the waste thermal inkjet resistor (320) based on an output of the sensor (104). That is, the component controller (322) may independently activate/deactivate the different thermal inkjet resistors. For example, when the sensor (104) detects a cell to be analyzed, the component controller (322) may activate the cell thermal inkjet resistor (318) and may either deactivate the waste thermal inkjet resistor (320) or allow it to run. Similarly, when the sensor (104) does not detect the presence of a cell to be analyzed, the component controller (322) may deactivate the cell thermal inkjet resistor (318) and may activate the waste thermal inkjet resistor (320). Thus, a cell presence-based sorting mechanism is described that effectively sorts cells on an individual, rather than aggregate, resolution, thus enhancing yield. All this is done while maintaining a contaminant free and gentle environment.

Figure 4A:
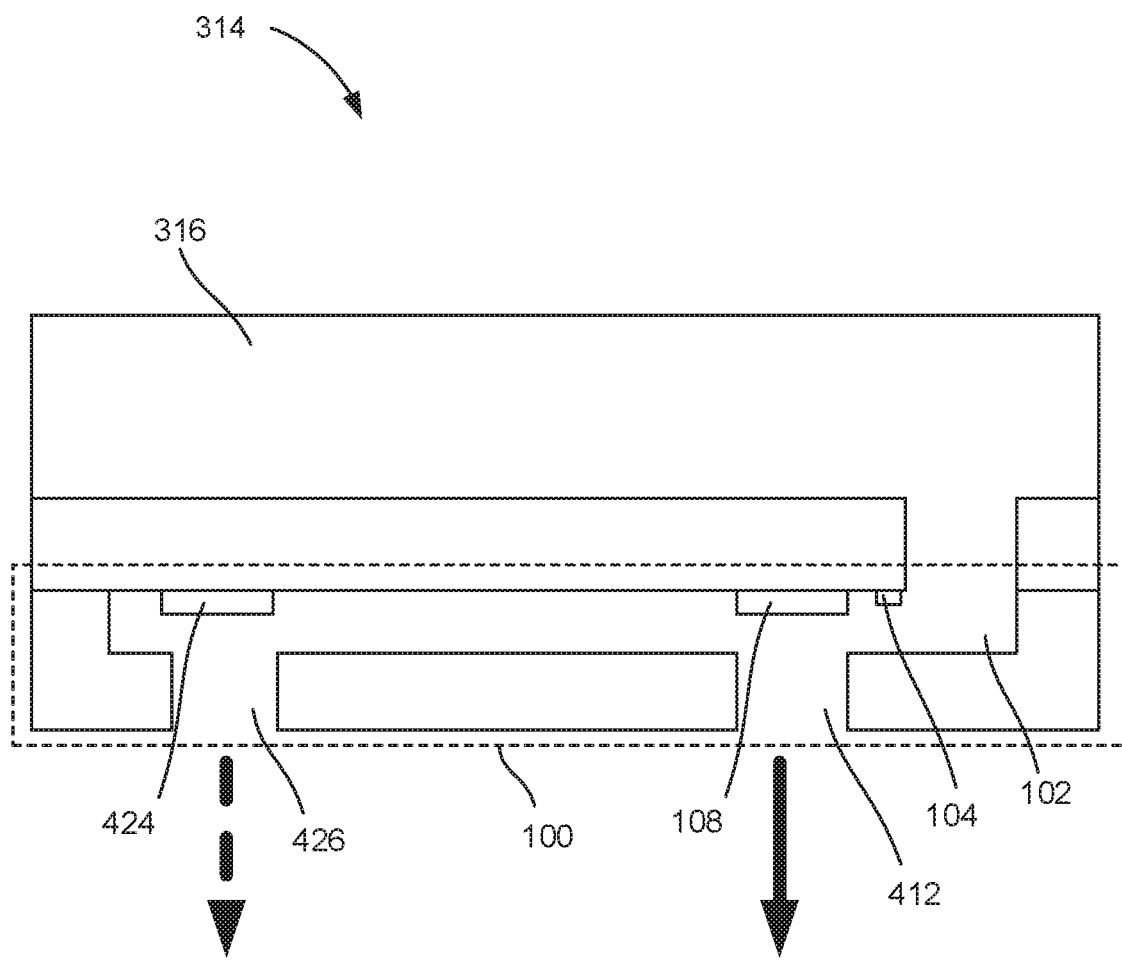
FIGS. 4A-4D are diagrams of a cell sorting system, according to an example of the principles described herein.
Figure 4B:
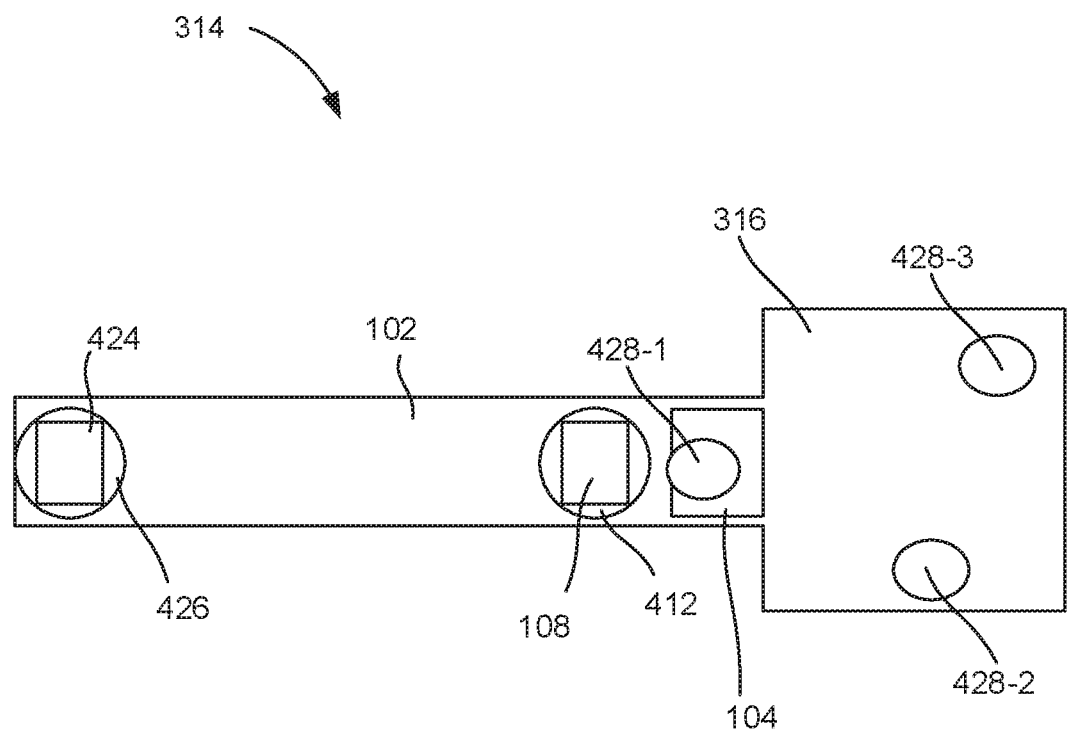
Figure 4C:
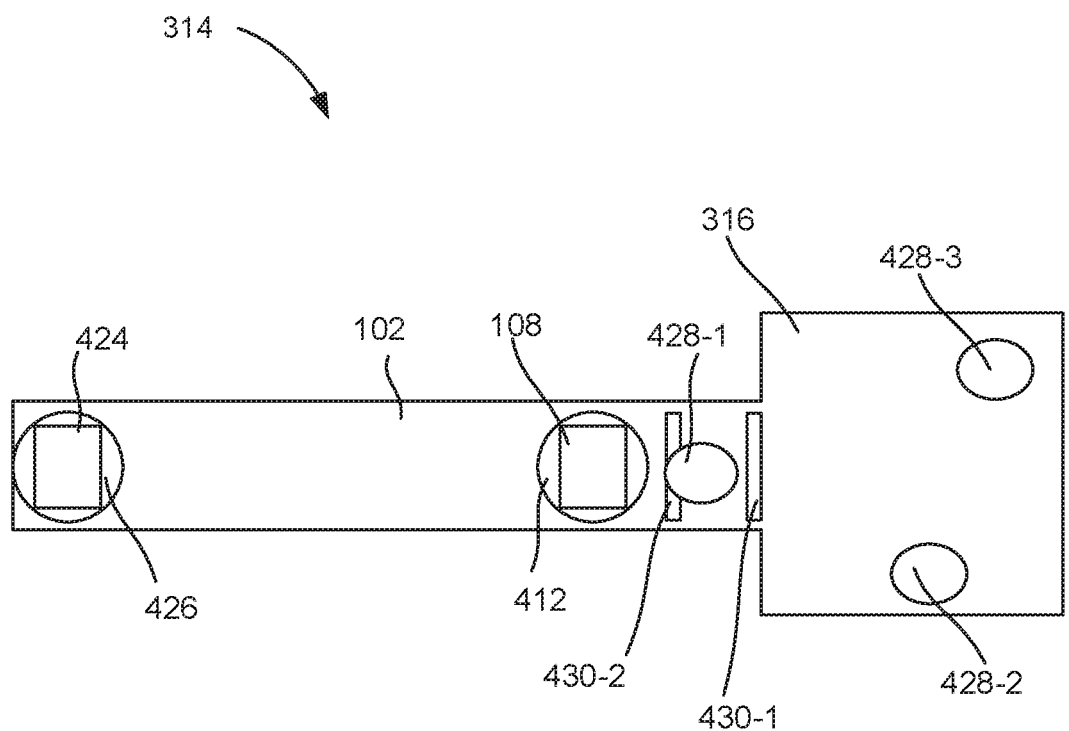
Figure 4D:
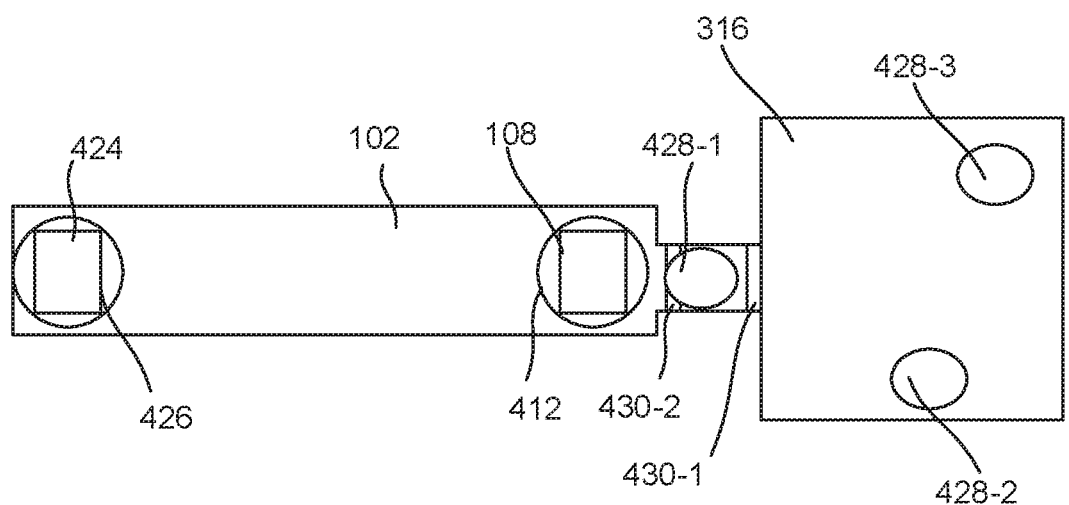

FIGS. 4A-4D are diagrams of a cell sorting system (314), according to an example of the principles described herein. Specifically, FIG. 4A depicts a cross-sectional diagram of the cell sorting system (314) and FIGS. 4B-4D are underside views of the cell sorting system (314) with different layouts. As described above, the cell sorting system (314) may either 1) eject the waste fluid to an external waste reservoir or 2) transport the waste fluid to an internal waste reservoir. FIGS. 4A-4D depict the former. That is, in this example, the waste transport device (FIG. 1, 110) is at least one waste ejector (424) to eject, through a waste orifice (426), the waste fluid from the cell sorting system (314).

An example of fluid flow through the cell sorting system (314) is now described. In this example, a sample, such as a blood sample, is held in a cell reservoir (316). Due to action of the ejectors (108, 424), or due to environmental conditions, the blood sample flows into the microfluidic channel (102). As it flows, the sample and its constituent cells pass by the sensor (104) which as described may be any type of sensor (104) to differentiate and detect cells to be analyzed based on any number of criteria. In one example, the waste ejector (424) is continually or periodically firing. Then, once a cell to be analyzed is detected, for example a bacterial cell, the component controller (FIG. 3, 322) of the cell sorting system (314) activates the cell ejector (108) to eject the bacterial cell through the orifice (412) as depicted by the solid arrow into a downstream structure such as a microwell plate. In this example, once a bacterial cell to be analyzed is detected, the component controller (FIG. 3, 322) may deactivate the waste ejector (424).

In other examples, the waste ejector (424) continues to eject waste fluid through a waste orifice (426) onto a waste reservoir. In these examples, the waste ejector (424) may operate continually throughout the entire sample sorting operation.

By comparison, once a cell that is not to be analyzed is detected, for example a blood cell, the component controller (FIG. 3, 322) of the cell sorting system (314) deactivates the cell ejector (108) to let the blood cell pass by without ejection through the orifice (312). In this example, the waste ejector (424) is active to eject the blood cell through a waste orifice (426) as indicated by the dashed arrow onto a waste reservoir. In these examples, the waste ejector (424) may operate continually throughout the entire sample sorting operation.

FIG. 4B depicts an underside view of one example of the cell sorting system (314). FIG. 4B depict the cells (428) as they reside in the cell reservoir (316) and as they pass through the cell sorting system (314). As described above, the cells (428-1, 428-2, 428-3) may be passed single-file through the microfluidic channel (102) such that each is individually sorted. FIG. 4B depicts a single sensor (104) that is adjacent the cell ejector (108) and the orifice (412) and also depicts the waste ejector (424) and the waste orifice (426) through which waste fluid is ejected.

FIG. 4C depicts an underside view of one example of the cell sorting system (314). In the example depicted in FIG. 4C, the sensor (FIG. 1, 104) is an impedance sensor that includes electrode plates (430-1, 430-2) separated by a gap. As described above, in this example, cells (428) are sorted based on their electrical conductivity as determined by an impedance detected between the electrode plates (430-1, 430-2).

FIG. 4D depicts an underside view of one example of the cell sorting system (314). In the example depicted in FIG. 4D, the sensor (FIG. 1, 104), which in this case is a pair of electrode plates (430-1, 430-2) separated by a gap, is disposed in a region of the microfluidic channel (102) that has a cross-sectional area that is reduced as compared to the rest of the cross-sectional area of the microfluidic channel (102). This constriction simplifies the detection of cells (428) as the entirety of the sensing area is filled with the cell (428) and there is less space for carrier fluid. That is, the constriction, by reducing the effect of carrier fluid on the sensor (FIG. 1, 104), amplifies the sensed characteristic that is used to distinguish cells (428) as they pass by. That is, the impedance of a solution is affected by both the cells (428) and the carrier fluid present. The constriction, by reducing the amount of carrier fluid, ensures that any sensed impedance is more directly mapped to the cell (428) itself, and not to the cell/solution combination. Thus, a higher resolution sorting process is possible.

Figure 5A:
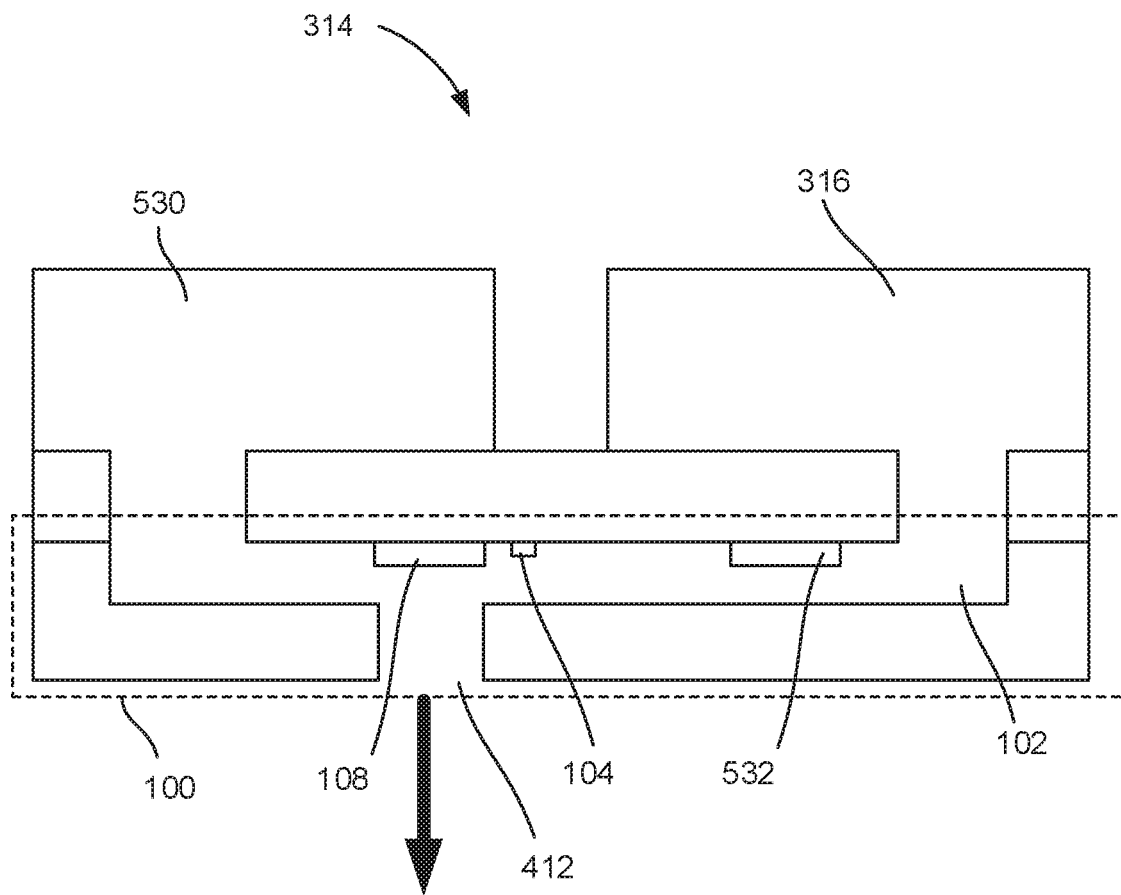
FIGS. 5A-5B are diagrams of a cell sorting system, according to another example of the principles described herein.
Figure 5B:
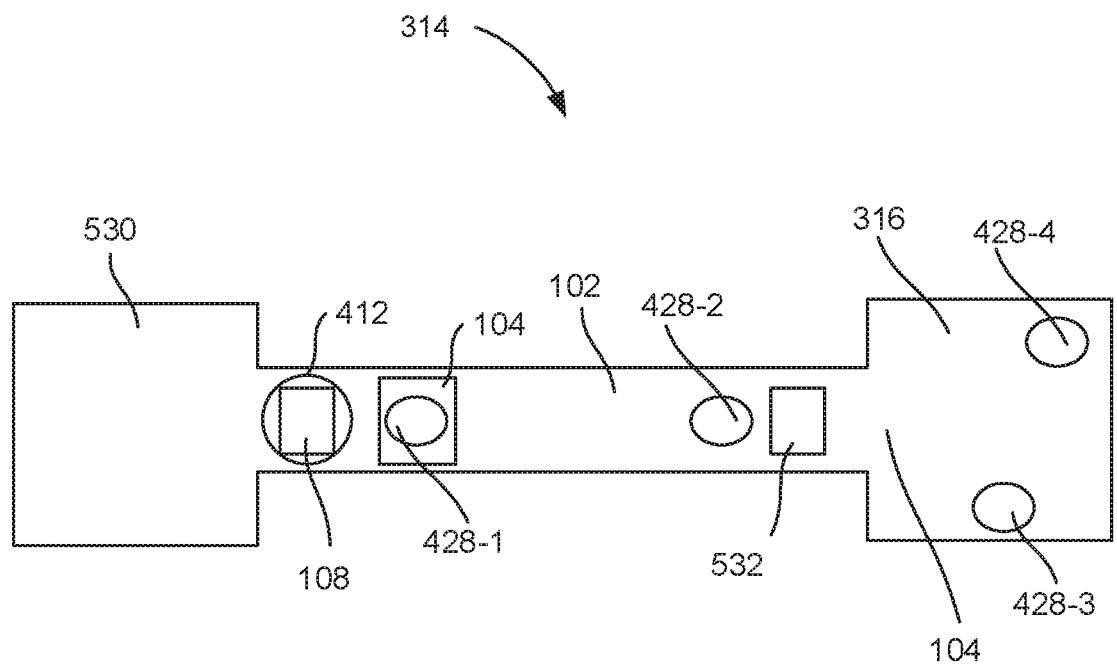

FIGS. 5A-5B are diagrams of a cell sorting system (314), according to another example of the principles described herein. Specifically, FIG. 5A depicts a cross-sectional diagram of the cell sorting system (314) and FIG. 5B is an underside view of the cell sorting system (314). As described above, the cell sorting system (314) may either 1) eject the waste fluid to an external waste reservoir or 2) transport the waste fluid to an internal waste reservoir. FIGS. 5A and 5B depict the latter. That is in this example, the cell sorting system (314) includes, in a single substrate, the cell reservoir (316) and a waste reservoir (530).

In this example, rather than having multiple orifices (412, FIG. 4, 426), the cell sorting system (314) includes a single orifice (412) through which cells (428) to be analyzed are ejected. Waste fluid by comparison passes by the orifice (412) and travels into the waste reservoir (530). The waste reservoir (530), like the cell reservoir (316) may be disposed above the cell sorting device (FIG. 1, 100).

In the example depicted in FIGS. 5A and 5B, the waste transport device (FIG. 1, 110) is an integrated pump (532) disposed in the microfluidic channel (102) to move fluid through the cell sorting device (100) towards the waste reservoir (530). Similar to the cell ejector (108), the integrated pump (532) may be a firing resistor or other thermal device, a piezoelectric element, or other mechanism for moving fluid through the microfluidic channel (102).

An example of fluid flow through the cell sorting system (314) is now described. In this example, a sample, such as a blood sample, is held in a cell reservoir (316). Due to action of the cell ejector (108) and integrated pump (532), or due to environmental conditions, the blood sample flows into the microfluidic channel (102). As it flows, the sample and its constituent cells (428) pass by the sensor (104). Once a cell (428) to be analyzed is detected, for example a bacterial cell, the component controller (FIG. 3, 322) of the cell sorting system (314) activates the cell ejector (108) to eject the bacterial cell through the orifice (412) as depicted by the solid arrow into a downstream structure such as a microwell plate.

By comparison, once a cell (428) that is not to be analyzed is detected, for example a blood cell, the component controller (FIG. 3, 322) of the cell sorting system (314) deactivates the cell ejector (108) to let the blood cell pass by without ejection through the orifice (412). In both cases, i.e., when a cell (428) to be analyzed is present or not, the integrated pump (532) operates to draw fluid through the microfluidic channel (102). However, when the cell ejector (108) is deactivated, the fluid, i.e., the blood cells, are passed into the waste reservoir (530).

FIG. 5B depicts an underside view of one example of the cell sorting system (314). FIG. 5B depict the cells (428) as they reside in the cell reservoir (316) and as they pass through the cell sorting system (314). As described above, the cells (428-1, 428-2, 428-3, 428-4) may be passed single-file through the microfluidic channel (102) such that each is individually sorted. FIG. 5B depicts a single sensor (104) that is adjacent the cell ejector (108) and the orifice (412) and also depicts the integrated pump (532) and the waste reservoir (530) which collects the waste fluid.

Figure 6A:
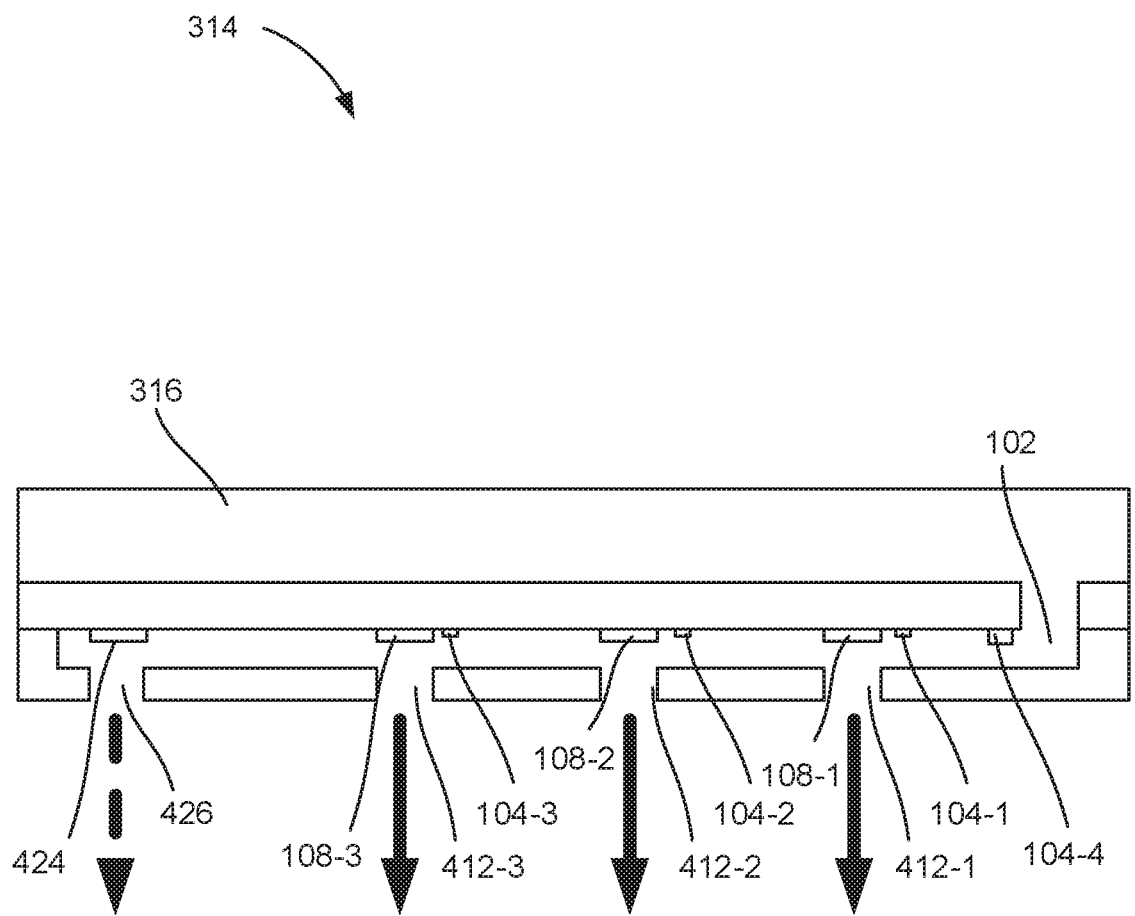
FIGS. 6A-6B are diagrams of a cell sorting system, according to another example of the principles described herein.
Figure 6B:
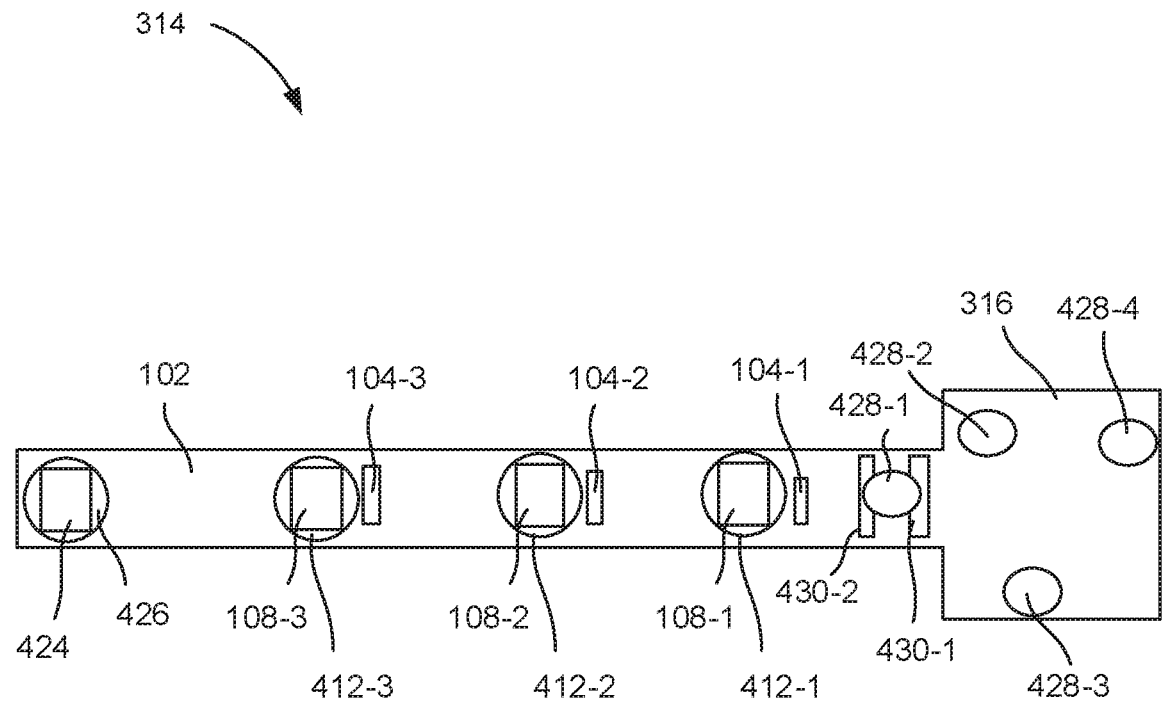

FIGS. 6A-6B are diagrams of a cell sorting system (314), according to another example of the principles described herein. Specifically, FIG. 6A depicts a cross-sectional diagram of the cell sorting system (314) and FIG. 6B is an underside view of the cell sorting system (314). In this example, rather than having a single sorting device (FIG. 1, 100), the cell sorting system (314) includes multiple cell sorting devices (FIG. 1, 100), each of which is disposed under the cell reservoir (316). That is, the cell sorting system (314) includes multiple cell ejectors (108-1, 108-2, 108-3), which in some examples indicates that the at least one cell thermal inkjet resistor (FIG. 3, 318) includes multiple cell thermal inkjet resistors (FIG. 3, 318). Moreover, each cell sorting device (FIG. 1, 100) includes a sensor (104-1, 104-2, 104-3) per cell thermal inkjet resistor (FIG. 3, 318). In some cases, in addition to sensors (104) per ejector (108), the cell sorting system (314) includes an additional sensor (104-4) that is upstream of all of the ejectors (108). In this example, the additional upstream sensor (104-4) may determine the cell type while the individual per-ejector (108) sensors (104-1, 104-2, 104-3) are sensors that do not determine a cell type, but rather just determine the presence or absence of the cell, to determine whether the respective ejector (108) should be activated to eject a cell. Such a multi-sensor system accounts for differential flows. That is, a cell may slow down (by sampling different, slower streamlines) or get stuck temporarily along the way to the ejector (108) and relying on just the upstream sensor (104-4) may lead to mis-timed activation of the ejectors (108).

In this example, each cell thermal inkjet resistor (FIG. 3, 318) is individually controllable. That is an output of a particular sensor (104) may trigger activation of a corresponding cell ejector (108), and just that cell ejector (108). In some examples, each sensor (104) is to determine a presence of a different type of cell (FIG. 4B, 428). That is, the component controller (FIG. 3, 322) may compare the outputs of the different sensors (104) to different threshold values such that each corresponding cell ejector (108) activates independently of a different cell ejector (108). In the example depicted in FIGS. 6A and 6B, the waste transport device (FIG. 1, 110) is at least one waste ejector (424) to eject, through a waste orifice (426), the waste fluid from the cell sorting system (314).

An example of fluid flow through the cell sorting system (314) is now described. In this example, a sample, such as a blood sample, is held in a cell reservoir (316). Due to action of the ejectors (108, 424), or due to environmental conditions, the blood sample flows into the microfluidic channel (102). As it flows, the sample and its constituent cells (FIG. 4B, 428) pass by the first sensor (104-1). Then, once a first type of cell (FIG. 4B, 428) is detected, for example a bacterial cell, the component controller (FIG. 3, 322) of the cell sorting system (314) activates the first cell ejector (108-1) to eject the bacterial cell through the first orifice (112-1) as depicted by the solid arrow into a downstream structure such as a microwell plate. As described above, detection of a bacterial cell may or may not trigger deactivation of the waste ejector (424). As a cell (FIG. 4B, 428) that is not to be analyzed is detected, for example a blood cell, the component controller (FIG. 3, 322) of the cell sorting system (314) deactivates the first cell ejector (108-1) to let the blood cell pass by without ejection through the first orifice (112-1).

Then, once a second type of cell (FIG. 4B, 428) is detected by the second sensor (104-2), for example a blood cell, the component controller (FIG. 3, 322) of the cell sorting system (314) activates the second cell ejector (108-2) to eject the blood cell through the second orifice (112-2) as depicted by the solid arrow into a downstream structure such as a microwell plate. As described above, detection of a blood cell may or may not trigger deactivation of the waste ejector (424). As a cell (FIG. 4B, 428) that is not to be analyzed are detected, the component controller (FIG. 3, 322) of the cell sorting system (314) deactivates the second cell ejector (108-2) to let the additional cells and/or carrier fluid pass by without ejection through the second orifice (112-2).

The third sensor (104-3) may operate similarly to identify and sort a third type of cell (FIG. 4B, 428) with waste fluid being transported towards, and ejected by the waste ejector (424). Thus, the cell sorting system (314) provides for the distinction of any number of cells (FIG. 4B, 428) and for the separation of those cells (FIG. 4B, 428).

FIG. 6B depicts an underside view of one example of the cell sorting system (314). FIG. 6B depict the cells (428) as they reside in the cell reservoir (316) and as they pass through the cell sorting system (314). As described above, the cells (428-1, 428-2, 428-3, 428-4) may be passed single-file through the microfluidic channel (102) such that each is individually sorted. FIG. 6B also depicts the multiple cell ejectors (108), sensors (104), and orifices (412), as well as the waste ejector (424) and waste orifice (426). FIG. 6B also depicts an example where the cell sorting system (314), in addition to sensors (104) per cell ejector (108), also includes a sensor upstream of all the cell ejectors (108), which upstream sensor includes a pair of electrode plates (430-1, 430-2).

Figure 7A:
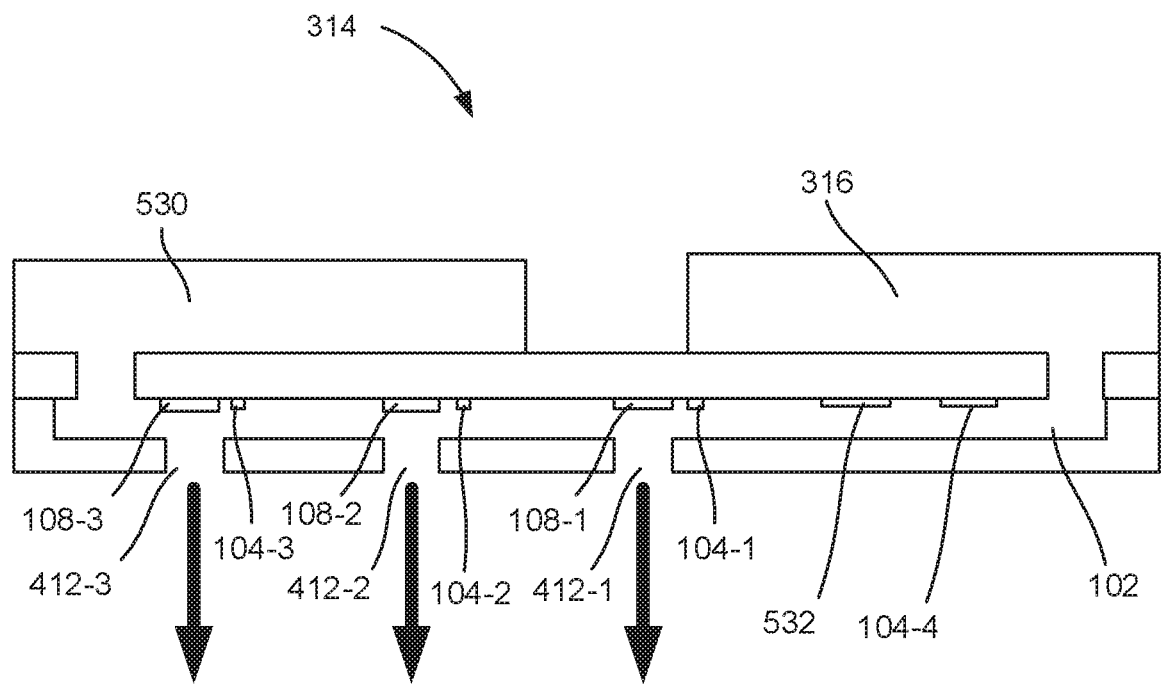
FIGS. 7A-7B are diagrams of a cell sorting system, according to another example of the principles described herein.
Figure 7B:
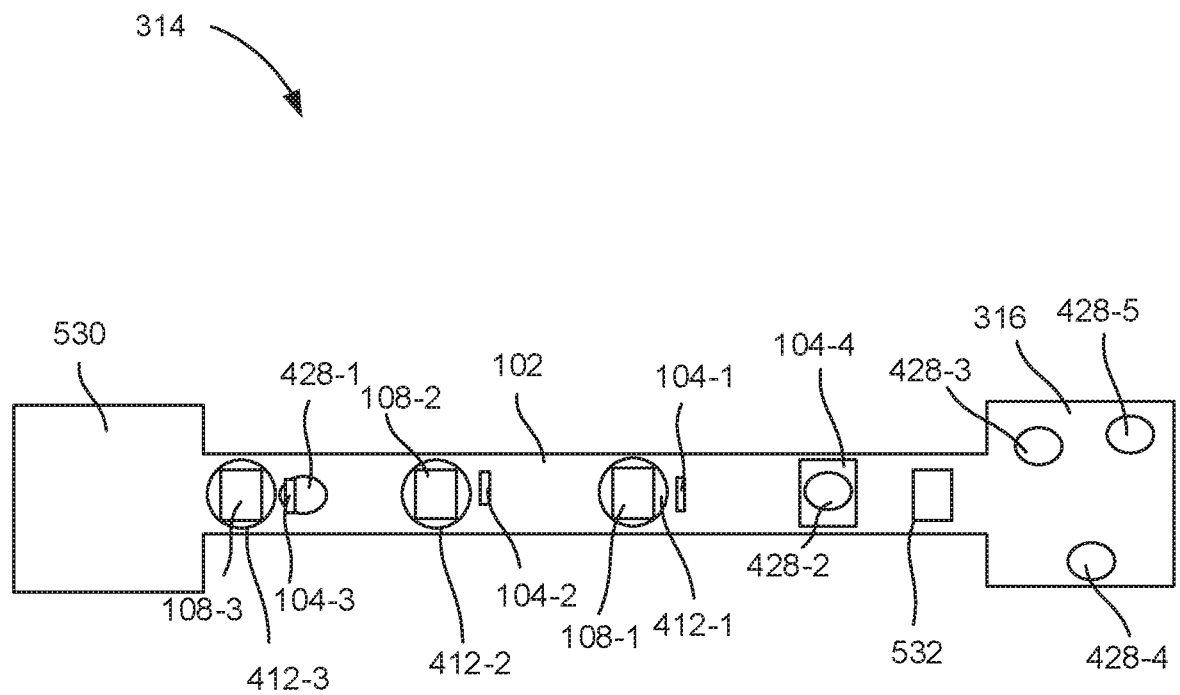

FIGS. 7A-7B are diagrams of a cell sorting system (314), according to another example of the principles described herein. Specifically, FIG. 7A depicts a cross-sectional diagram of the cell sorting system (314) and FIG. 7B is an underside view of the cell sorting system (314). In this example, rather than having a single sorting device (FIG. 1, 100), the cell sorting system (314) includes multiple cell sorting devices (FIG. 1, 100), each of which is disposed under the cell reservoir (316). That is, the cell sorting system (314) includes multiple cell ejectors (108-1, 108-2, 108-3), which in some examples indicates that the at least one cell thermal inkjet resistor (FIG. 3, 318) includes multiple cell thermal inkjet resistors (FIG. 3, 318). Moreover, each cell sorting device (FIG. 1, 100) includes a sensor (104-1, 104-2, 104-3) per cell thermal inkjet resistor (FIG. 3, 318).

In this example, each cell thermal inkjet resistor (FIG. 3, 318) is individually controllable. That is, an output of a particular sensor (104) may trigger activation of a corresponding cell ejector (108) and just that cell ejector (108). In some examples, each sensor (104) is to determine a presence of a different type of cell (FIG. 4B, 428). That is, the component controller (FIG. 3, 322) may compare the outputs of the different sensors (104) to different threshold values such that each corresponding cell ejector (108) activates independently of other cell ejectors (108). In the example depicted in FIGS. 7A and 7B, the waste transport device (FIG. 1, 110) is at least one integrated pump (532) direct waste fluid towards a waste reservoir (530) that is in the same chip as the cell reservoir (316).

An example of fluid flow through the cell sorting system (314) is now described. In this example, a sample, such as a blood sample, is held in a cell reservoir (316). Due to action of the ejectors (108) and integrated pump (532), or due to environmental conditions, the blood sample flows into the microfluidic channel (102). As it flows, the sample and its constituent cells (FIG. 4B, 428) pass by the first sensor (104-1). Then, once a first type of cell (FIG. 4B, 428) is detected, for example a bacterial cell, the component controller (FIG. 3, 322) of the cell sorting system (314) activates the first cell ejector (108-1) to eject the bacterial cell through the first orifice (112-1) as depicted by the solid arrow into a downstream structure such as a microwell plate.

As a cell (FIG. 4B, 428) that is not to be analyzed is detected, for example a blood cell, the component controller (FIG. 3, 322) of the cell sorting system (314) deactivates the first cell ejector (108-1) to let the blood cell pass by without ejection through the first orifice (112-1).

Then, once a second type of cell (FIG. 4B, 428) is detected by the second sensor (104-2), for example a blood cell, the component controller (FIG. 3, 322) of the cell sorting system (314) activates the second cell ejector (108-2) to eject the blood cell through the second orifice (112-2) as depicted by the solid arrow into a downstream structure such as a microwell plate. As cell that is not to be analyzed are detected, the component controller (FIG. 3, 322) of the cell sorting system (314) deactivates the second cell ejector (108-2) to let the additional cells and/or carrier fluid pass by without ejection through the second orifice (112-2). The third sensor (104-3) may operate similarly to identify and sort a third type of cell with waste fluid being transported towards the waste reservoir (530). Thus, the cell sorting system (316) provides for the distinction of any number of cells and for the separation of those cells.

FIG. 7B depicts an underside view of one example of the cell sorting system (314). FIG. 7B depict the cells (428) as they reside in the cell reservoir (316) and as they pass through the cell sorting system (314). As described above, the cells (428-1, 428-2, 428-3, 428-4, 428-5) may be passed single-file through the microfluidic channel (102) such that each is individually sorted. FIG. 7B also depicts the multiple cell ejectors (108), sensors (104), and orifices (112), as well as the integrated pump (532) and the waste reservoir (530) which collects the waste fluid. FIG. 7B also depicts an example where the cell sorting system (314), in addition to sensors (104) per cell ejector (108), also includes a sensor upstream of all the cell ejectors (108).

Figure 8:
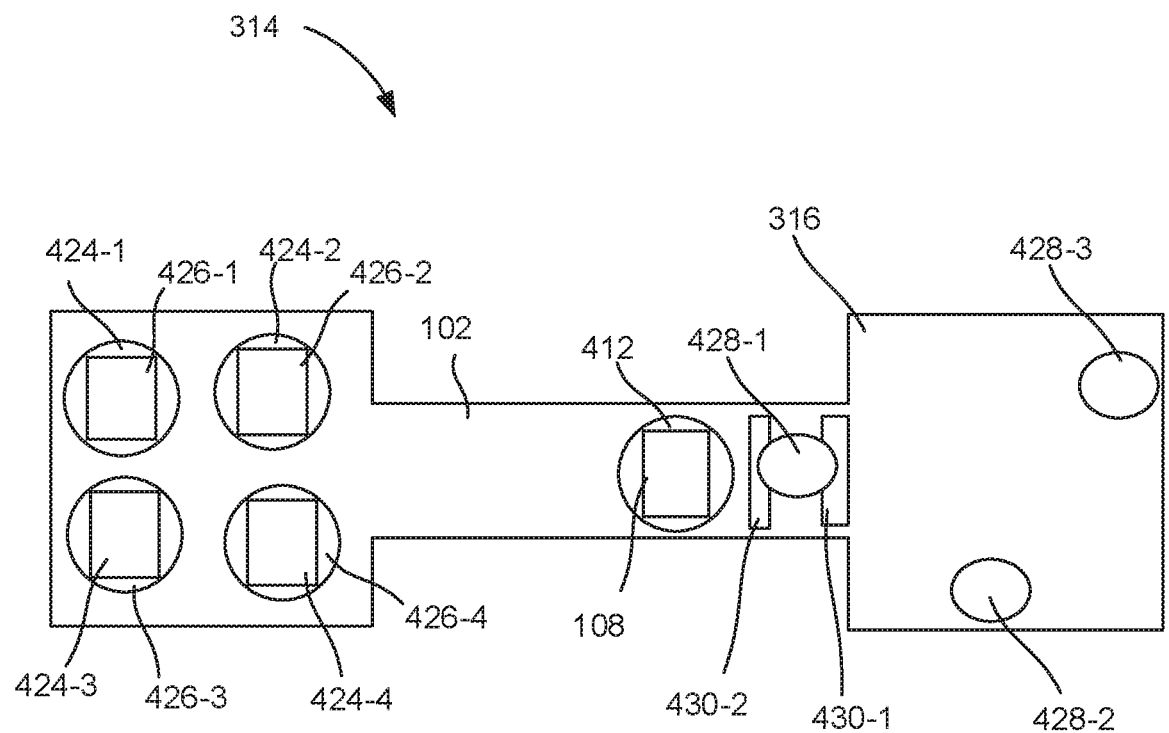
FIG. 8 is a diagram of a cell sorting system, according to an example of the principles described herein.

FIG. 8 is a diagram of a cell sorting system (314), according to an example of the principles described herein. In the example depicted in FIG. 8, the at least one waste ejector (424) includes multiple waste ejectors (424). Specifically, as a sample in a cell reservoir (316) may have a large amount of carrier fluid as compared to the cells (428) to be analyzed, a large amount of waste fluid may be generated following operation of the cell ejector (108). Accordingly, the cell sorting system (314) may include an array of waste ejectors (424-1, 424-2, 424-3, 424-4) that eject waste fluid through respective orifices (426-1, 426-2, 426-3, 426-4). Thus, waste fluid may be removed at a faster rate in part to prevent backup of waste fluid in the microfluidic channel (102). While FIG. 8 depicts a particular configuration of waste ejectors (424) and waste orifices (426) any configuration may be implemented in accordance with the principles described herein.

Figure 9:
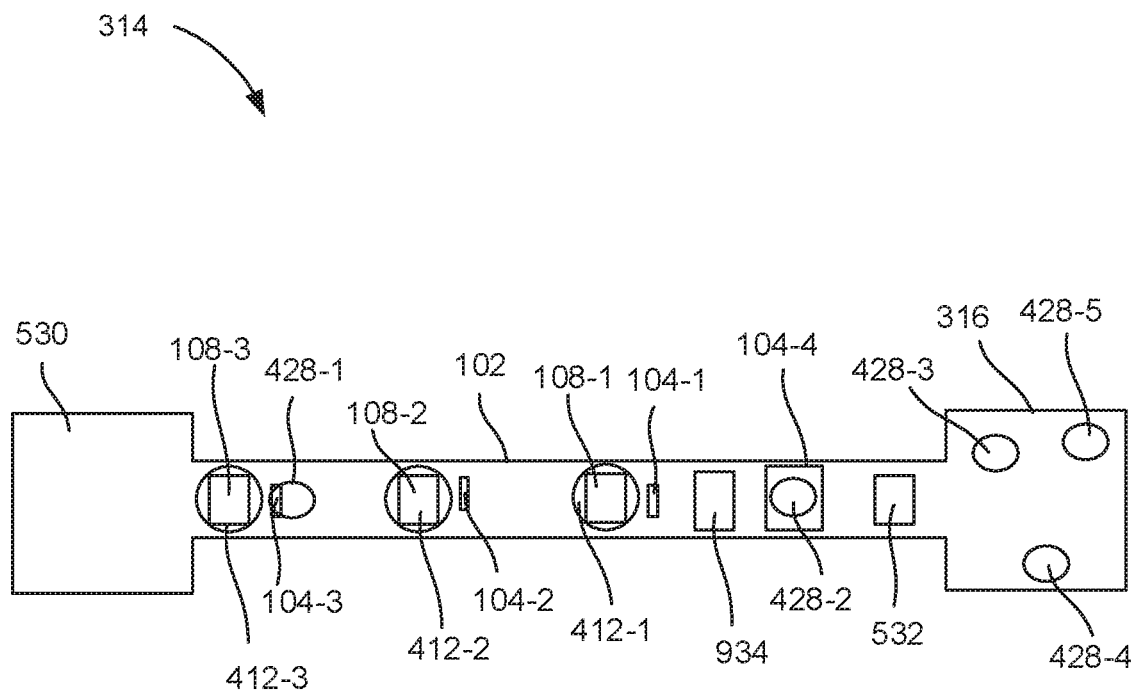
FIG. 9 is a diagram of a cell sorting system, according to an example of the principles described herein.

FIG. 9 is a diagram of a cell sorting system (314), according to an example of the principles described herein. In the example depicted in FIG. 9, an additional sensor is disposed in the cell sorting system (314). That is, in addition to individual sensors (104) paired with associated ejectors (108) and the upstream sensor (104-4) disposed upstream of all the ejectors (108), the cell sorting system (314) includes an additional sensor such as a flow sensor (934). The flow sensor (934) may detect a flow rate. When used in conjunction with the cell presence sensor (104-4) placed at an entry of the microfluidic channel (102) additional precision regarding the timing of cell ejector (108) actuation is provided. For example, knowing when a particular cell passes by the upstream sensor (104-4) and knowing the flow rate of the fluid past the flow sensor (934), it can be determined with precision, when the cell ejector (108) intended to eject the particular cell (428), should be activated.

In summary, using such a cell sorting system 1) allows single cell sorting of a sample; 2) uses fluid ejection to separate cells from carried fluid; 3) uses two separate ejection devices spatially separated from each other; 4) separates cells without use of an alteration inducing stain; and 5) simplifies the device integration into a larger system. However, the devices disclosed herein may address other matters and deficiencies in a number of technical areas.

What is claimed is:

1. A cell sorting device, comprising:
 a microfluidic channel to serially transport individual cells from a volume of cells along a flow path;
 a sensor disposed in the microfluidic channel to distinguish between a cell to be analyzed and waste fluid; and
 at least two fluid transport devices disposed within the microfluidic channel, the at least two fluid transport devices comprising:
  multiple thermal inkjet resistors to, responsive to detection of a cell to be analyzed, eject the cell to be analyzed from the cell sorting device, wherein each cell thermal inkjet resistor is individually controllable; and
  a waste transport device to direct the waste fluid to a waste reservoir, wherein the cell sorting device comprises a sensor per cell thermal inkjet resistor.

2. The cell sorting device of claim 1, wherein the waste transport device comprises at least one waste ejector to eject, through a waste orifice, the waste fluid from the cell sorting device.

3. The cell sorting device of claim 2, wherein the waste ejector operates independently of the sensor.

4. The cell sorting device of claim 2, wherein responsive to detection of a cell to be analyzed, the waste ejector is deactivated.

5. The cell sorting device of claim 1, wherein the waste transport device is an integrated pump disposed in the microfluidic channel to move fluid through the cell sorting device towards a waste reservoir.

6. The cell sorting device of claim 5, wherein the waste reservoir is on the same substrate as a cell reservoir.

7. The cell sorting device of claim 1, wherein the sensor is selected from:
 an impedance sensor;
 an optical sensor;
 a flow sensor;
 a thermal sensor;
 a pressure sensor;
 a magnetic sensor; and
 a sensor to detect a marker placed on the cell to be analyzed.

8. The cell sorting device of claim 1, wherein the sensor is disposed in a region of the microfluidic channel that has a reduced cross-sectional area.

9. A method, comprising:
 passing, in serial fashion, a quantity of cells from a cell reservoir to at least one cell sorting device of a microfluidic cell analysis system; and
 for each cell sorting device:
  detecting cells to be analyzed;
  activating a thermal inkjet resistor of multiple thermal inkjet resistors of the cell sorting device, when a cell to be analyzed is detected, to eject the cell to be analyzed, wherein each cell thermal inkjet resistor is individually controllable; and directing a waste fluid to a waste reservoir, wherein each cell sorting device comprises a sensor per cell thermal inkjet resistor.

10. The method of claim 9, wherein cells to be analyzed are distinguished from other cells based on at least one of:
a cell size;
a cell impedance;
a cell color;
a cell fluorescence; and
a cell light scattering response.

11. A cell sorting system, comprising:
a cell reservoir to contain a volume of cells;
multiple cell sorting devices, each cell sorting device comprising:
a microfluidic channel to serially transport individual cells from the cell reservoir along a flow path;
a sensor to distinguish between a cell to be analyzed and waste fluid;
at least two fluid transport devices disposed within the microfluidic channel, the at least two fluid transport devices comprising:
multiple thermal inkjet resistors to, responsive to detection by the sensor of a cell to be analyzed, activate to eject the cell to be analyzed, wherein each cell thermal inkjet resistor is individually controllable; and
a waste thermal inkjet resistor to eject waste fluid through an orifice to a waste reservoir, wherein each cell sorting device comprises a sensor per cell thermal inkjet resistor; and
a component controller configured to selectively activate the cell thermal inkjet resistor and the waste thermal inkjet resistor based on an output of the sensor.

12. The cell sorting system of claim 11, wherein the multiple sorting devices are disposed underneath the cell reservoir.

13. The cell sorting system of claim 11, wherein each sensor per cell thermal inkjet resistor is to determine a presence of a different type of cell.

* * * * *